(12) United States Patent
Groke et al.

(10) Patent No.: US 9,282,914 B2
(45) Date of Patent: Mar. 15, 2016

(54) COMPREHENSIVE MEDICAL SYSTEM FOR MAGNETIC NAVIGATION

(71) Applicants: David Groke, Nürnberg (DE); Michael Wiets, Erlangen (DE)

(72) Inventors: David Groke, Nürnberg (DE); Michael Wiets, Erlangen (DE)

(73) Assignee: SIEMENS AKTIENGESELLSCHAFT, München (DE)

( * ) Notice: Subject to any disclaimer, the term of this patent is extended or adjusted under 35 U.S.C. 154(b) by 126 days.

(21) Appl. No.: 14/010,882

(22) Filed: Aug. 27, 2013

(65) Prior Publication Data
US 2014/0081291 A1  Mar. 20, 2014

(30) Foreign Application Priority Data
Sep. 19, 2012  (DE) .......................... 10 2012 216 797

(51) Int. Cl.
 A61B 19/00 (2006.01)
 A61B 5/06 (2006.01)
 A61B 5/00 (2006.01)
 G01R 33/28 (2006.01)

(52) U.S. Cl.
 CPC ............... *A61B 5/062* (2013.01); *A61B 5/6805* (2013.01); *A61B 19/2203* (2013.01); *A61B 2019/2253* (2013.01); *A61B 2019/2261* (2013.01); *G01R 33/285* (2013.01)

(58) Field of Classification Search
 CPC ........... A61B 19/2203; A61B 19/5244; A61B 2019/5251; A61B 5/06; A61B 2019/2253; A61B 19/20; A61B 2019/2261; A61B 5/062; A61B 5/6805; G01R 33/285
 USPC .......................................................... 606/130
 See application file for complete search history.

(56) References Cited

U.S. PATENT DOCUMENTS

| 5,993,375 | A  | * | 11/1999 | Engel ............................... 600/15 |
| 2008/0161679 | A1 | * | 7/2008 | von Jako et al. .............. 600/424 |
| 2009/0048484 | A1 |   | 2/2009 | Swain et al. |
| 2012/0197100 | A1 |   | 8/2012 | Arevalos |

FOREIGN PATENT DOCUMENTS

| CN | 2768163 Y | 3/2006 |
| CN | 101909541 A | 12/2010 |
| WO | WO 02/36047 * | 5/2002 |
| WO | WO 2009060460 A2 | 5/2009 |

OTHER PUBLICATIONS

Jamie L. Manson et al:, [Cu(HF2)(pyz)2]BF4(pyz=pyrazine): long-range magnetic ordering in a pseudo-cubi coordination polymer comprised of bridging HF2 and pyrazine ligands,Chem. Commun., 2006, pp. 4894-4896, URL: http://pubs.rsc.org/en/Content/ArticleLanding/2006/CC/b608791d.

(Continued)

*Primary Examiner* — Katherine M Shi

(57) ABSTRACT

For an improved use even with medical imaging a comprehensive medical system for magnetic navigation of an object with a magnetic element within a human body is provided, having a magnet apparatus for generating a variable magnetic field in the region of the object, wherein the magnet apparatus has a plurality of electromagnets, which electromagnets are disposed in a flexibly-embodied net type structure, which net-type structure is especially able to be disposed directly on the body such that it surrounds the object on four sides.

5 Claims, 3 Drawing Sheets

(56) References Cited

OTHER PUBLICATIONS

Antiferromagnetisches Polymer, Oct. 27, 2006, Source: Forschungszentrum Dresden-Rossendorf URL: http://www.pro-physik.de/details/news/1114625/Antiferromagnetisches__Polymer.html.

Spin-reorientation transition in Co/Pt multilayers on nanospheres, Phys. Rev. B77, 134415 (2008) URL: http://prb.aps.org/abstract/PRB/v77/i13/e134415.

* cited by examiner

COMPREHENSIVE MEDICAL SYSTEM FOR MAGNETIC NAVIGATION

CROSS REFERENCE TO RELATED APPLICATIONS

The present application claims priority to German application No. 102012216797.8 DE filed Sep. 19, 2012, the entire content of which is hereby incorporated herein by reference.

FIELD OF INVENTION

The invention relates to a comprehensive medical system for magnetic navigation according to the claims.

BACKGROUND OF INVENTION

With the aid of medical systems for magnetic navigation it is possible to navigate objects and instruments which are usually used in interventional procedures, such as ablation catheters for example, in a targeted manner to a specific point within the heart or another region in the human body. Magnetic navigation allows this even without constant visual checking through x-ray and/or fluoroscopy images. A known medical system for magnetic navigation has a magnet apparatus, e.g. in the form of two large permanent magnets or electromagnets. The objects and instruments, such as catheters for example, are equipped at their tips with one and/or more magnetic elements. The magnetic fields of the magnet apparatus are activated and thereby the magnetic field vector changed by means of a control apparatus so that the object can be automatically navigated to any given positions. To this end in the case of permanent magnets these can be mechanically moved for example and in the case of electromagnets these can be supplied with power accordingly and the magnetic field changed in this way.

Imaging methods in which magnetic navigation has previously not been able to be used because of various disadvantages are primarily Computed Tomography (CT) or Magnetic Resonance Tomography (MRT). Limiting factors here for example are the closed construction of the CT scanner, which does not allow large permanent magnets e.g. a known system made by Stereotaxis, or large electromagnets of a system made by Magnetecs Systems for example to be positioned at the height of the required isocenter (e.g. the heart). With MR systems the greatest limiting factor is the strong magnetic field of the MR system, which does not allow large metal objects to be brought into the immediate vicinity. In addition an MR system also generally has a closed construction, so that here too the same limiting factor applies as with a CT scanner.

With known permanent magnets (e.g. Stereotaxis) the magnetic field vector of the magnetic field will be moved purely by a geometrical change of the magnets, which by contrast with a change of the field of electromagnets, takes a very long time. Permanent magnets can be built in an open design, so that for example good access by a doctor to the patient can be achieved; but permanent magnets are structurally very complex and large. This scarcely enables steep angulations to be set at the imaging system, e.g. C-arm (e.g. Stereotaxis Niobe system with maximum ±30° RAO/LAO). With permanent magnets there is also a danger from all magnetic objects which are bought too close to the permanent magnets.

With electromagnets the magnetic field vector of the magnetic field can be set relatively quickly and above all silently. The constructional outlay is not as great as with permanent magnets but here too steep angulations of much greater than 35° cannot be set at the imaging system. In addition no laminar air flow is possible either, which limits the use of electromagnets in a sterile environment.

The heavy weight of permanent magnets and electromagnets means that in some cases floor reinforcement measures must be taken, which renders installation difficult and expensive. In addition not every room is suitable for conversion since other devices such as air-conditioning systems, elevators etc. can be disturbed by the vibrations. Current magnets are of very large size. This is conditional on the access that one wishes to and must grant the doctor for carrying out an intervention. The large size means that the distance to the isocenter becomes very large. As a result of the inverse square law the magnetic field decreases proportionally with the increasing distance at $1/r^2$. To be adapted to this distance (magnet <-> ROI) enormously large magnets are needed.

SUMMARY OF INVENTION

The object of the present invention is to provide a medical system for magnetic navigation which both guarantees rapid and reliable navigation of objects in the body of a patient as well as offering easy access to the patient.

The object is achieved in accordance with the invention by a medical system for magnetic navigation in accordance with the claims. Advantageous embodiments of the invention are the subject matter of the associated dependent claims in each case.

The inventive comprehensive medical system for magnetic navigation of an object with a magnetic element within a human body has a magnet apparatus for generating a variable magnetic field in the area of the object, wherein the magnet apparatus has a plurality of electromagnets, which electromagnets are disposed in a flexibly embodied net-type structure, and which net-type structure is able to be disposed especially directly on the body so that it surrounds the object from four sides. The invention enables magnetic navigation of an object to be carried out in a simple manner and with customary precision and simultaneously enables access to the patient to be greatly improved, since huge magnets with a great constructional outlay do not have to be disposed as in known systems, but a flexible net-type structure merely has to be disposed directly on the patient or around the patient. A plurality of small electromagnets, which can be activated accordingly for magnetic navigation, is disposed at the node points of the net-type structure. The plurality of small electromagnets generates a magnetic field which, through changes, allows the object to be navigated by means of a magnetic element in the body. Since the net-type structure is embodied flexibly it can be disposed directly in the immediate vicinity of the patient, especially directly around the latter. Access to the patient is guaranteed by the net-type nature of the structure.

In accordance with an embodiment of the invention the electromagnets are able to be activated individually and are embodied to allow their magnetic field strength to be changed. In this way the magnetic field can be controlled and regulated in any given way within the net-type structure for each point, so that a precise navigation of the object to an exact point is possible.

To activate the electromagnet such that the object is able to be moved by means of magnetic navigation within the body, the comprehensive system has a control apparatus.

In accordance with a further embodiment of the invention the net-type structure is embodied as a type of tube. In this way it can be put onto or covered over the patient in the form of a "vest" There can be provision for example for manufacturing the net-type structure in different sizes in order to be able to use individual "vests" for patients of different shapes. In this way the electromagnets lie especially firmly and tightly against the patient body and an especially precise setting of the magnetic field and thus navigation of the object is possible.

In accordance with a further embodiment of the invention the net-type structure features cutouts. In this way access is additionally provided, by which a doctor can gain surgical access to the patient for example.

In an advantageous manner for the use of the comprehensive system in an MR system the electromagnets are embodied from a non-metallic magnetic material.

BRIEF DESCRIPTION OF THE DRAWINGS

The invention and also further advantageous embodiments in accordance with features of the dependent claims are explained in greater detail below with reference to schematically presented exemplary embodiments, without this producing a restriction of the invention to these exemplary embodiments. In the figures:

DETAILED DESCRIPTION OF INVENTION

Figure 1:
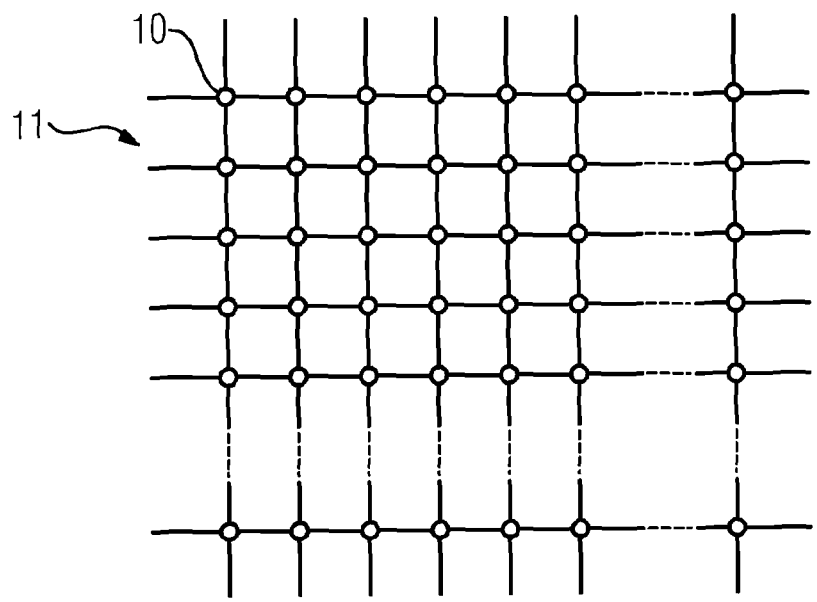
FIG. 1 shows an overhead view of an inventive net-type structure of a comprehensive medical system for magnetic navigation.
Figure 2:
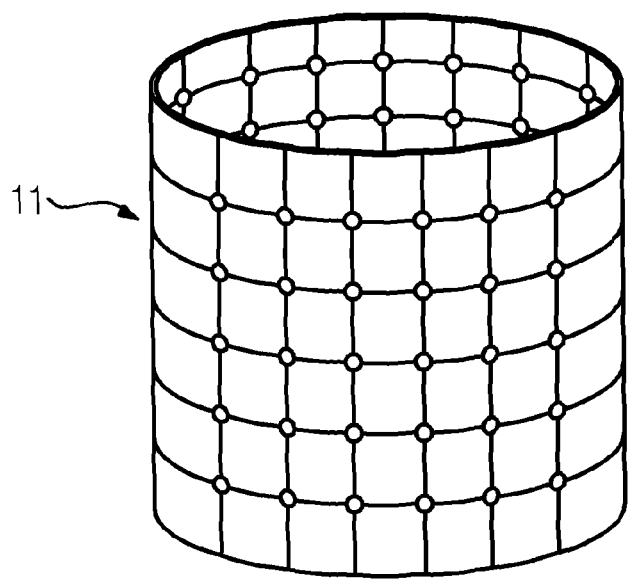
FIG. 2 shows a view of a net-type structure of a comprehensive medical system for magnetic navigation embodied as a type of tube.
Figure 4:
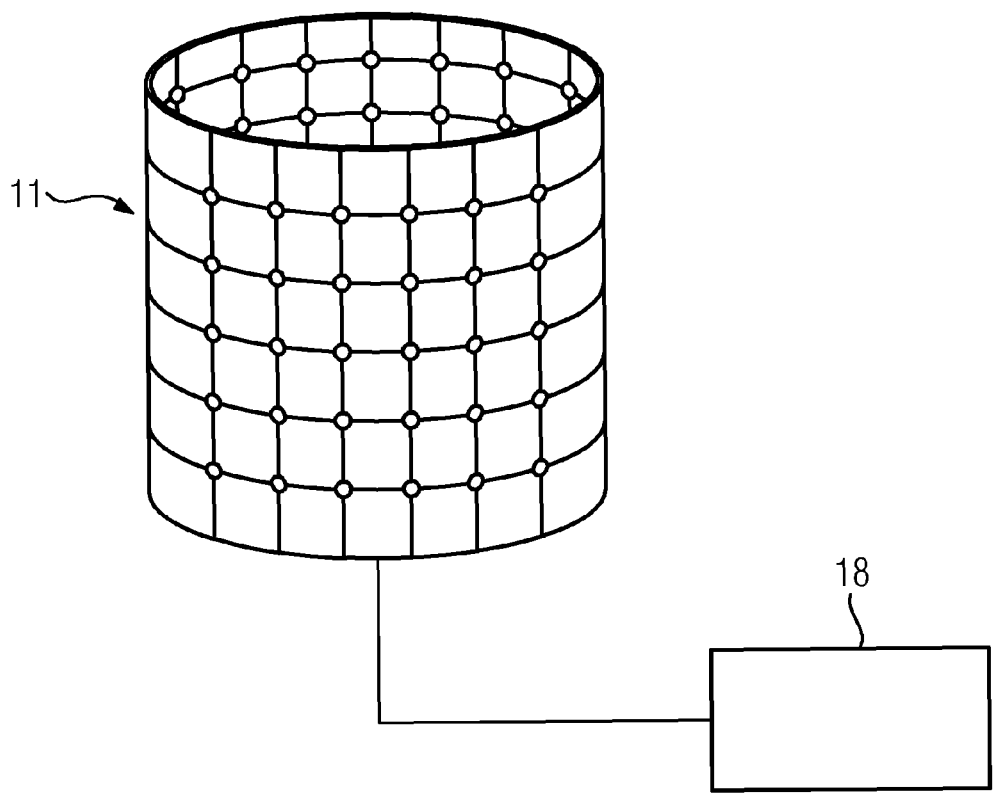
FIG. 4 shows a view of a comprehensive medical system for magnetic navigation.
Figure 6:
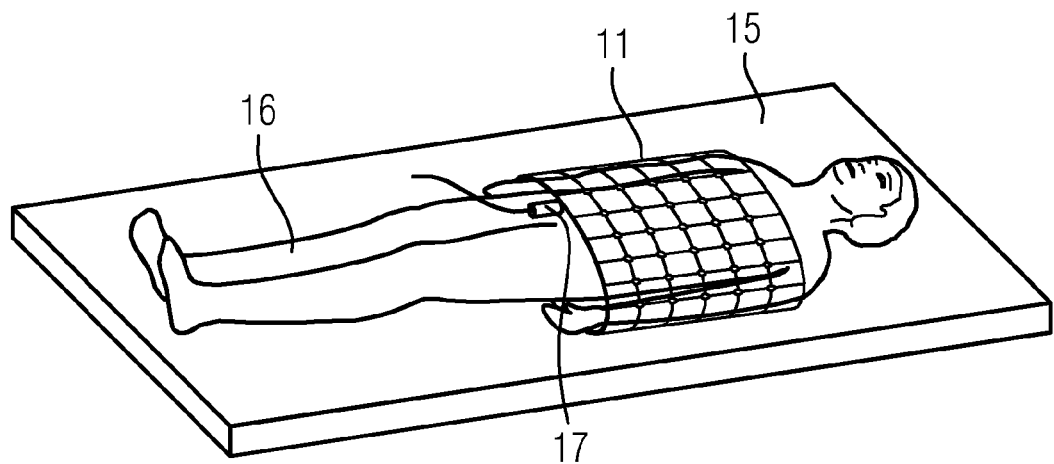
FIG. 6 shows a side view of a patient with a net-type structure of a comprehensive medical system for magnetic navigation.

FIG. 1 shows an overhead view of a section of a magnet apparatus in the form of a net-type structure 11 of an inventive comprehensive medical system for magnetic navigation. The net-type structure 11 has meshes and can be formed for example from a flexible but stable plastic material. Small electromagnets 10 are disposed evenly in each case at the node points of the meshes or at other defined points of the net-type structure. The net-type structure 11, as shown in FIG. 2, is embodied as a type of tube or vest. This enables it to be easily pulled over a patient, e.g. like a vest. In FIG. 6 a patient 16, who is wearing a vest-shaped net-type structure 11 with electromagnets 10, is shown on a patient couch 15. The electromagnets 10 are also distributed as evenly as possible on the net-type structure 11 adapted to the patient. The electromagnets 10 can be activated by means of a control apparatus 18—shown in FIG. 4—e.g. by the voltage applied being able to be continuously varied. The electromagnets are disposed such that a magnetic field is generated within the space formed by the net-type structure 11 and the magnetic field and the magnetic field vector can be changed at any point in this space in any given manner.

The net-type structure 11 is laid around the patient or pulled onto them. If an object with a magnetic element, e.g. an instrument, a catheter 17—as shown in FIG. 6—or a capsule is present in the body of the patient, then the object can be navigated in any given way by changing the magnetic field. A magnetic field can also be generated by the electromagnets during an intervention on the patient. The arrangement of the electromagnets on the net-type structure is such that very small movements, changes in direction or maintaining the object exactly at a point in the patient are possible. This can for example be achieved by a simultaneous activation of a number of electromagnets at different field strengths.

The net-type structure, by comparison with the magnet facilities of known comprehensive medical systems for magnetic navigation, is disposed very close to the patient and the ROI (Region of Interest). This has many advantages: It means that the comprehensive magnet apparatus does not have to generate such a strong magnetic field as known systems, since it is generated very close to the required point (least squares law $I \propto 1/r^2$, wherein I is the radiation intensity and r is the distance). The magnet apparatus is a small unit, is thus less expensive to construct and is also financially more attractive than known systems. The danger of accidents with magnetic objects is also smaller since this only exists close to the net-type structure. The meshes of the net-type structure and the small space requirement make access to the patient possible for a doctor, e.g. for an intervention or OP.

Figure 5:
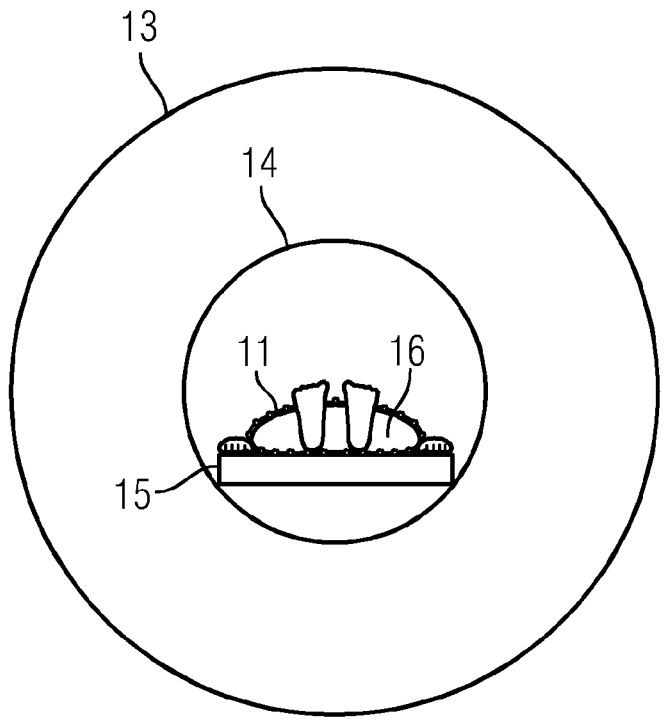
FIG. 5 shows a view of a CT scanner with a patient wearing a net-type structure of a comprehensive medical system for magnetic navigation.

Because of the small space requirement of the inventive comprehensive medical system for magnetic navigation, imaging x-ray methods, e.g. by means of C-arms, can also be used in different, even steep angulations)(>45° and magnetic navigation can also be carried out within a Computed Tomography device. FIG. 5 shows for example how a patient 16 on a patient couch 15 is placed in the opening 14 of a CT device 13. Here he can wear the net-type structure 11 without restrictions and a magnetic navigation of an object in the body of the patient 16 can be carried out in a simple manner. The use of electromagnets makes possible a very fast switchover and thus a very fast change in the magnetic field for navigation.

Figure 3:
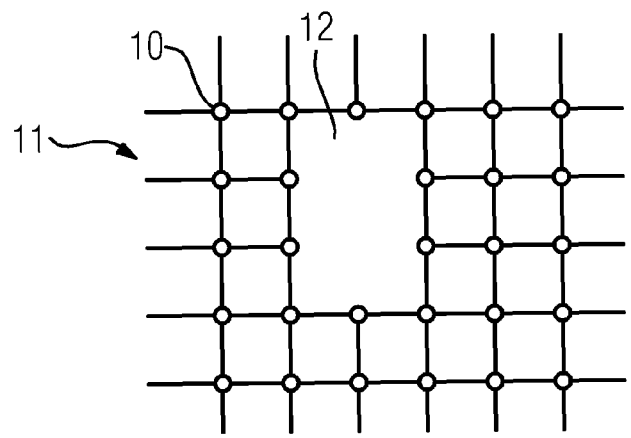
FIG. 3 shows a view of a cutout in a net-type structure.

FIG. 3 shows a net-type structure 10 which allows an additional access 12, which is formed by cutting away meshes and one or more electromagnets. Such access 12 also makes it easier for a doctor to carry out interventions.

In accordance with a further embodiment of the invention the electromagnets 12 are embodied from a non-metallic magnetic material. This makes it possible to also perform magnetic navigation within a magnetic resonance scanner Thus known organic materials and polymers or materials with a small proportion of metal but with magnetic properties exist. The electromagnets can be embodied from this type of non-metallic material. Furthermore the two magnetic fields used ("net" and MR) should be synchronized in order to avoid interference in both directions.

The magnet apparatus, i.e. the net-type structure 11, can for example even be manufactured as a single-use product or as a reusable product. It is conceivable to provide different sizes of net-type structure for different sizes of patient. Furthermore the net-type structure can be implemented as a tube able to be adapted to different sizes, which is laid around the patient and subsequently adapted to the body (like a shrink-wrap tube). This type of the implementation minimizes a movement within the net-type structure and thus an undesired change of the magnetic field and maximum positional accuracy is achieved.

The previous systems for magnetic navigation have each only made possible either the most unrestricted access to the patient possible (e.g. Stereotaxis) or a rapid change in direction, e.g. of the catheter. The inventive comprehensive system for magnetic navigation combines the two advantages.

The invention can be briefly summarized in the following way: For an improved use even with medical imaging a comprehensive medical system for magnetic navigation of an object with a magnetic element within a human body is provided, having a magnet apparatus for generating a variable magnetic field in the region of the object, wherein the magnet apparatus has a plurality of electromagnets, which electromagnets are disposed in a flexibly-embodied net-type structure, which net-type structure is especially able to be disposed directly on the body such that it surrounds the object on four sides.

We claim:

1. A comprehensive medical system for magnetic navigation of an object with a magnetic element within a human body, comprising:
    a magnet apparatus for generating a variable magnetic field in the region of the object,
    wherein the magnet apparatus has a plurality of electromagnets,
    wherein the electromagnets are disposed in a flexibly embodied net-type structure,
    wherein the flexible net-type structure is able to be disposed directly on the body such that it surrounds the object on four sides, and
    wherein the flexible net-type structure is embodied as a shrink-wrap tube that is able to be laid around the body.

2. The comprehensive system as claimed in claim 1, wherein the plurality of electromagnets are embodied for individual activation and are embodied variable in their magnetic field strength.

3. The comprehensive system as claimed in claim 1, further comprising an activation apparatus for activating the plurality of electromagnets such that the object is able to be moved by means of magnetic navigation within the body.

4. The comprehensive system as claimed in claim 1, wherein the net-type structure includes cutouts.

5. The comprehensive system as claimed in claim 1, wherein the plurality of electromagnets are embodied from a non-metallic magnetic material.

* * * * *